(12) United States Patent
Holmqvist

(10) Patent No.: US 11,571,521 B2
(45) Date of Patent: Feb. 7, 2023

(54) MEDICAMENT DELIVERY DEVICE COMPRISING A LOCKING MECHANISM HAVING A LEVER

(71) Applicant: SHL Medical AG, Zug (CH)

(72) Inventor: Anders Holmqvist, Värmdo (SE)

(73) Assignee: SHL MEDICAL AG, Zug (CH)

( * ) Notice: Subject to any disclaimer, the term of this patent is extended or adjusted under 35 U.S.C. 154(b) by 490 days.

(21) Appl. No.: 16/687,181

(22) Filed: Nov. 18, 2019

(65) Prior Publication Data

US 2020/0101235 A1 Apr. 2, 2020

Related U.S. Application Data

(63) Continuation of application No. 15/601,742, filed on May 22, 2017, now Pat. No. 10,653,849, which is a (Continued)

(30) Foreign Application Priority Data

Apr. 5, 2011 (SE) .................................... 1150300-0

(51) Int. Cl.
*A61M 5/32* (2006.01)
*A61M 5/20* (2006.01)

(52) U.S. Cl.
CPC ........ *A61M 5/3202* (2013.01); *A61M 5/2033* (2013.01); *A61M 5/3257* (2013.01); *A61M 2005/208* (2013.01)

(58) Field of Classification Search
CPC .............. A61M 5/2033; A61M 5/3243; A61M 5/3257; A61M 5/326; A61M 2005/2013;
(Continued)

(56) References Cited

U.S. PATENT DOCUMENTS 6,419,658 B1 * 7/2002 Restelli ................. A61M 5/326
604/110
2002/0169421 A1 * 11/2002 McWethy ........... A61M 5/3271
604/228
(Continued)

FOREIGN PATENT DOCUMENTS

| CN | 201752522 U | 3/2011 |
|---|---|---|
| WO | 0247746 A1 | 6/2002 |

(Continued)

OTHER PUBLICATIONS

Sweden Patent Office, International Search Report in PCT/SE2012/050355 dated Jul. 4, 2012.
(Continued)

*Primary Examiner* — Kami A Bosworth
(74) *Attorney, Agent, or Firm* — McDonnell Boehnen Hulbert & Berghoff LLP

(57) ABSTRACT

Medicament delivery device comprising a movable guard (10) being movable between a proximal and a distal position and a locking mechanism (15) having a lever (16), the lever (16) restricting movement of an actuation locking member (24) until the movable guard is positioned in a distal position and the lever (16) restricting movement of the guard (10) in a proximal position after actuation of the device.

19 Claims, 6 Drawing Sheets

Related U.S. Application Data continuation of application No. 14/009,942, filed as application No. PCT/SE2012/050355 on Mar. 30, 2012, now Pat. No. 9,737,668.

(60) Provisional application No. 61/471,886, filed on Apr. 5, 2011.

(58) Field of Classification Search
CPC .... A61M 2005/2026; A61M 2005/206; A61M 2005/2073; A61M 2005/208; A61M 2005/3247; A61M 2005/3258; A61M 2005/3261; A61M 2005/3263; A61M 2005/3267; A61M 2005/3268
See application file for complete search history.

(56) References Cited

U.S. PATENT DOCUMENTS

| | | | | |
|---|---|---|---|---|
| 2003/0028149 A1* | 2/2003 | Sanpietro | ............... | A61M 5/326 604/110 |
| 2003/0050607 A1* | 3/2003 | Gagnieux | ............. | A61M 5/326 128/919 |
| 2003/0105430 A1 | 6/2003 | Lavi et al. | | |
| 2004/0236287 A1* | 11/2004 | Swenson | ........... | A61M 25/0637 604/177 |
| 2005/0171477 A1* | 8/2005 | Rubin | .................... | A61M 5/326 604/156 |
| 2005/0203466 A1* | 9/2005 | Hommann | .......... | A61M 5/2033 604/240 |
| 2006/0189938 A1 | 8/2006 | Hommann et al. | | |

FOREIGN PATENT DOCUMENTS

| | | | | |
|---|---|---|---|---|
| WO | 2004060445 A2 | 7/2004 | | |
| WO | WO-2006111862 A1 * | 10/2006 | .......... | A61M 5/2033 |
| WO | 2006118616 A1 | 11/2006 | | |
| WO | 2009152542 A1 | 12/2009 | | |

OTHER PUBLICATIONS

Sweden Patent Office, Written Opinion in PCT/SE2012/050355 dated Jul. 4, 2012.

English Translation of Abstract of Chinese Patent Application No. CN 201752522 dated May 22, 2017.

* cited by examiner

MEDICAMENT DELIVERY DEVICE COMPRISING A LOCKING MECHANISM HAVING A LEVER

CROSS REFERENCE TO RELATED APPLICATIONS

The present application is a Continuation of U.S. patent application Ser. No. 15/601,742 filed on May 22, 2017, now issued as U.S. Pat. No. 10,653,849, which is a continuation of U.S. patent application Ser. No. 14/009,942 filed Oct. 4, 2013, now issued as U.S. Pat. No. 9,737,668, which is a 35 U.S.C. 371 National Application of PCT/SE2012/050355 filed Mar. 30, 2012, which claims the benefit of U.S. Provisional Patent Application No. 61/471,886 filed Apr. 5, 2011 which claims priority to Swedish Patent Application No. 1150300-0 filed Apr. 5, 2011, the entire contents of which are incorporated entirely herein by reference.

TECHNICAL FIELD

The present invention relates to a medicament delivery device, for example for injection, having a locking mechanism. More specifically, the present invention relates to a medicament delivery device for auto-injection having a mechanism for inhibiting dose delivery until the device is positioned at a dose delivery site and/or for locking a guard in a proximal position after a dose is delivered, the mechanism comprising a ledge.

RELATED ART

Medicament delivery devices for automatic or semi-automatic injection of medicaments have been known for many years. While the first generations of injectors merely aimed to deliver a medicament as quickly as possible, increased use of the devices by patients in non-clinical settings has lead to the necessity of providing further handling and safety functions.

Important handling and safety functions of medicament delivery devices include inhibiting premature actuation of the device (misfiring). To ensure that the medicament is properly injected, actuation of the device is inhibited until the auto-injector is correctly positioned at a dose delivery site. Furthermore, since the member delivering the medicament can be sharp and may be contaminated after the device has been actuated, devices that retract or cover the medicament delivery member when the device is withdrawn from the dose delivery site have been developed. To prevent that a person unintentionally contacts the medicament delivery member and to allow safely discarding the device, some devices feature a mechanism that locks the device once the medicament delivery member is covered or retracted.

WO 02/047746 discloses a medicament delivery device comprising a housing arranged to contain a medicament container, a needle cover surrounding a needle and spring means. The spring means may push the needle past the end of the needle cover and operate the medicament container to supply a dose of medicament. Furthermore, the device comprises first locking means locking the spring means in a pressurized state. The first locking means may be released by first activating means, which may be manually operated. The first activating means are locked by second locking means, which are released by second activating means when the needle cover is exposed to pressure by the medicament delivery device being positioned at the dose delivery site. When the patient withdraws the injector from the dose delivery site, further spring means push the needle cover out of the housing. A lock ring having arms that engage openings in the housing is provided to prevent the needle cover being pushed in again. Although the medicament delivery device provides all necessary functions, several mechanism are necessary to achieve this objective.

WO 2004/060445 discloses a safety system for a syringe. The system may forcefully inject a syringe when an actuator contacts the dose delivery site and withdraw the syringe into a housing when injection is completed. However, the needle and the guard can be moved, allowing for the needle to be contacted even after it is retracted into the housing. Therefore, WO 2004/060445 proposes the use of end covers for safe disposal of the system.

WO 2006/118616, which relates to a needle-less injector device, discloses a mechanism for inhibiting actuation of the device until the device is positioned against the skin. However, also in this case the mechanism disclosed is not designed to prevent users or third persons from unintentionally contacting the medicament delivery member after the device is actuated.

As shown above, available medicament delivery devices do either not provide the necessary handling and safety functions or require cooperation of one or several complex mechanisms. Therefore, some of the present devices are not safe, while others are costly to produce and difficult to assemble. Accordingly, there is a need for medicament delivery devices that comprise mechanisms providing some or all of these functions with as few parts as possible and in a reliable manner.

SUMMARY OF THE INVENTION

In order to overcome one or several of the above-mentioned problems, medicament delivery device according to the independent claims are provided.

Further aspects, improvements and variations are disclosed in the dependent claims, the figures and the description.

The medicament delivery device of the present invention allows inhibiting actuation of the device until the device is positioned at a dose delivery site. Furthermore, a medicament delivery device is provided wherein the medicament delivery member is safely covered after actuation of the device. The device can thus be stored or discarded in a safe way. These advantages are achieved by providing a medicament delivery device with an improved locking mechanism. The locking mechanism of the inventive medicament delivery device provides one or several of the functions in a reliable and safe manner and requires a minimal amount of elements. The locking mechanism is easy to assemble and the medicament delivery device can be manufactured cost-effectively.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

According to independent claim 1, a medicament delivery device is provided. The medicament delivery device comprises a moveable guard that is movable between a proximal position and a distal position and a locking mechanism having a lever. The lever restricts or locks the movement of an actuation locking member until the movable guard is positioned in a distal position and the lever restricts or locks the movement of the guard in a proximal position after the device is actuated. So, both of these functions may be provided by a single locking mechanism, e.g., a lever. The lever may be a seesaw.

According to a further embodiment of the present invention, a medicament delivery device for auto-injection comprises a movable guard being movable between a proximal and a distal position and a locking mechanism having a see-saw is provided. The see-saw restricts movement of an actuation locking member until the movable guard is positioned in a distal position and/or the see-saw restricts movement of the guard in a proximal position after the device is actuated. Any feature described below may also be provided with this embodiment of the invention. In particular, any feature relating to the lever may equally be provided for the see-saw.

The lever or the see-saw may be pivotally mounted in any member of the medicament delivery device. Preferably, the lever or the see-saw is formed integrally and pivotally with any member of the device. More preferably, the lever or the see-saw is formed integrally with a medicament container holder. The lever or the see-saw preferably is provided such that it can be pivoted or deflected around its pivotal axis in both directions.

In the context of the present invention, the term "guard" denominates a member for covering a medicament delivery member. The guard preferably is contacted when the device is positioned at the dose delivery site. Furthermore, the guard preferably covers the medicament delivery member when the device is withdrawn from the dose delivery site at least after the device has been actuated. Preferably, after actuation of the device the guard is moved to and locked in a position covering the medicament delivery member. Hence, the guard according to the invention is movable or displaceable. More preferably, after the device has been actuated, the guard is moved and locked in a proximal position when the device is withdrawn from the dose delivery site. The guard preferably is urged in a proximal direction by the force of a spring. The spring may be provided at the proximal end of the guard. The spring may be formed integrally with the guard. Thus, the guard is a protection element, such as a needle protection element or needle protection sleeve that protects the user against inadvertently or accidentally getting in contact with the needle which may be contaminated.

A medicament delivery member may be any member through which a medicament is delivered. For example, the medicament delivery member may be a needle or a nozzle, e.g., a needle-less injection nozzle. The medicament delivery member may be formed integrally with a medicament container or be an independent element of the device. Preferably, the medicament delivery member is covered or retracted until the medicament delivery device is actuated and may not be unintentionally contacted until this moment. For example, the medicament delivery member may be retracted in the medicament delivery device.

According to any embodiment of the present invention, the medicament delivery device may comprise an actuation mechanism and/or an actuation locking member. An actuation mechanism is a mechanism that actuates the device to deliver a dose. Preferably, the actuation mechanism actuates the device by releasing spring means from a pressurized state, the spring means being capable of pushing the medicament delivery member past the end of the needle cover and/or operating a medicament container to provide a dose of medicament. Preferably, the actuation mechanism actuates the device when activated by a user. The actuation mechanism preferably is activated when the user presses a push button. The push button may be located at the distal end of the device. In an example, the push button is pushable in a longitudinal direction of the medicament delivery device. In another example, the push button is first rotatable around the longitudinal axis of the medicament delivery device and subsequently pushable in longitudinal direction of the medicament delivery device. Instead of being in the form of a button, it may have the form of a sleeve. In another example, the push button is pushable transverse to the longitudinal axis of the medicament delivery device. Instead of a pushable button a rotary knob may be used.

In any embodiment of the present invention, the actuation mechanism preferably can only be activated when certain conditions are fulfilled. Preferably, the actuation mechanism is locked and can not be actuated until the device is positioned at a dose delivery site. For this purpose the device may comprise an actuation locking member locking actuation of the device. The actuation locking member may lock actuation of the device by locking the actuation mechanism and/or by locking another member and thereby inhibiting that the actuation mechanism is activated (e.g., unintentionally). Preferably, the actuation locking member locks actuation of the device by restricting the movement of a member or part of the actuation mechanism or of the entire actuation member. For example, the actuation locking member may have distally directed arms abutting protrusions of a member of the actuation mechanism.

When the actuation locking member restricts the movement of a member or part of the actuation mechanism, the actuation mechanism may be locked by restricting the movement of the actuation locking member. In any embodiment of the present invention the actuation mechanism and/or the actuation locking member may be provided such that actuation of the medicament delivery device is inhibited until the device is positioned at the dose delivery site. Preferably, actuation of the device is inhibited until a guard, e.g., a needle protection sleeve, that contacts the dose delivery site is moved or displaced and reaches a distal position.

According to any embodiment of the invention the actuation mechanism may comprise a medicament delivery drive unit for expelling the medicament from the medicament delivery device. The drive unit may include a plunger member. At least one spring for spring-loading the plunger member may be provided around the plunger member or in a hollow space thereof. The plunger member may be spring-loaded by the spring being compressed or elongated.

The medicament delivery drive unit may further comprise a drive spring holder for holding the compressed or elongated spring. The drive spring holder may be configured to partially surround the spring-loaded plunger member. Preferably, the drive spring holder is generally U-shaped and has at least one, preferably two proximally directed leg. Each leg may comprise a radial outwardly extending ledge.

The medicament delivery drive unit may further comprise connection means for holding the spring-loaded plunger member in a pre-loaded state. For this purpose the connection means may be arranged with a distally directed arm, which may be flexible in the radial direction. Preferably, the distal end of the arms is arranged with an inwardly directed hook. The hook may be configured to fit into at least one cut-out of the plunger member or a plunger rod. Preferably, two distally directed arms are provided, each having one inwardly directed hook. Preferably, the drive spring holder is axially arranged through the connection means.

Furthermore, the actuation mechanism may comprise at least one member of the actuation mechanism for releasing the connection means from the spring-loaded plunger member or the plunger rod. The member may be co-axially slidable on the connection means.

Preferably, the drive spring is compressed between a proximal inner end surface of the plunger member and drive spring holder when the medicament delivery drive unit is assembled. More preferably, the drive spring is compressed between a proximal inner end surface of the plunger member and a transversal contact end of the drive spring holder. The radial outwardly extending ledges of the of the drive spring holder may be engaged to the proximal annular surface of the connection means for preventing the drive spring holder from being moved in the distal direction by the spring. The member of the actuation mechanism may be arranged surrounding the distally directed arms of the connection means such that the hooks of the arms are engaged in a corresponding engagement with a cut-out on the plunger member.

Initial Position

According to any embodiment of the present invention, the movement of the actuation locking member may be restricted by a locking mechanism or a lever at least in a certain direction, preferably the proximal direction. Preferably, the movement of the actuation locking member is restricted when the lever is an initial position. The initial position preferably is the first position of a dose delivery cycle. More preferably, the initial position is a position in which the device is ready for being used but the actuation mechanism may not be activated. The initial position may be a position in which no force or substantially no force acts on the lever and/or in which the lever is not overlapped by members that may overlap the lever.

In order to restrict the movement of the actuation locking member, the lever may have any suitable shape. Preferably, the lever comprises at least one first portion and at least one second portion, the second portion being positioned further from a plane which is parallel to the longitudinal axis of the medicament delivery device and includes the pivotal axis about which the lever pivots than the first portion when the lever is in the initial position. Assuming a generally elongated or cylindrical shape of the medicament delivery device, said plane is a tangential plane to the outer surface of the medicament delivery device, i.e., of its housing, or parallel to such tangential plane. The second portion is raised or projected relative to said plane. For example, the lever may be curved or pivoted. More preferably, the lever comprises a second portion that is thicker than a first portion. Most preferably, the lever comprises a second portion having a ledge. The pivotal axis of the lever may be considered are border line or boundary between the first portion (being proximal form such line) and the second portion (being distal from the line).

According to any embodiment of the invention, it is preferred that the movement of the actuation locking member towards or into the position releasing the actuation mechanism is restricted by the actuation locking member abutting the lever when the lever is in the initial position. Preferably, the actuation locking member abuts at least a part of the second portion of the lever. More preferably, the movement of the actuation locking member is restricted because the actuation locking member abuts one of the portions of the lever that is thicker than the others. Most preferably, the movement of the actuation locking member is restricted by the actuation locking member abutting the ledge of the lever. Thus, the lever provides a locking function locking the actuation locking member in its initial position.

In any embodiment of the invention the actuation locking member preferably is provided distal of the lever. Accordingly, it is preferred that at least a part of the portion of the lever against which the actuation locking member abuts is provided at or close to the distal end of the lever. Preferably, at least a part of the second portion of the lever is provided distal of at least a part of the first portion of the lever, the second portion being positioned further from the plane that is generally parallel to the longitudinal axis of the medicament delivery device and including the pivotal axis about which the lever pivots than the first portion when the lever is in the initial position, as defined above. More preferably, at least a part of the second portion is provided distal of the pivotal axis of the lever and at least a part of the first portion is provided proximal of the pivotal axis of the lever. The pivotal axis is preferably perpendicular to the longitudinal axis of the medicament delivery device while being offset from the longitudinal axis. Assuming a generally elongated or cylindrical shape of the medicament delivery device, the pivotal axis may be a tangential to the outer surface of the medicament delivery device, i.e., of its housing, or parallel to such a tangential.

According to any embodiment of the invention, the guard preferably can be moved in at least one direction when the lever is in the initial position. Preferably, the guard can be moved in the distal direction. More preferably, the guard is moved in the distal direction when the medicament delivery device is pressed against the dose delivery site. Most preferably, the guard reaches a distal position when the medicament delivery device is correctly positioned at the dose delivery site. The guard preferably is moved in the distal direction against the force of a spring. The spring may be provided at the distal end. The spring may be integral with the guard.

Tensioned Position

When the guard moves, preferably, when the guard is moved or displaced in a distal direction, the guard or a member moved by the guard preferably overlaps at least a portion of the lever. Preferably, the guard or the member moved by the guard first overlaps at least a part of a first portion of the lever and subsequently overlaps at least a part of a second portion of the lever, the first portion being positioned closer to the plane which is generally parallel to the longitudinal axis of the medicament delivery device and includes the pivotal axis about which the lever pivots than the second portion when the lever is in the initial position, as defined above. Preferably, the guard or the member moved by the guard overlaps at least a part of the first portion that is provided proximal of the second portion first. More preferably, the guard or the member moved by the guard first overlaps a proximal portion of the lever and subsequently overlaps a distal portion of the lever. Most preferably, the guard or the member moved by the guard first overlaps at least a part of the first portion that is provided proximal of the pivotal axis of the lever and subsequently overlaps at least a part of the second that is positioned distal of the pivotal axis of the lever. Preferably, the lever has the general shape of a beam with a first and a second portion, the first portion being thinner than the second portion. When the guard or a member moved by the guard moves in a distal direction, preferably at least a part of the thinner portion that is provided proximal of the pivotal axis of the lever is overlapped first. Preferably, the guard slides over the lever, such as a sleeve. More preferably, the guard can slide over the second portion, the thicker portion or the ledge of the lever, because this portion and/or the portion of the guard or the member moved by the guard that contacts this portion is wedge-shaped.

Since the proximal portion of the lever is overlapped by the guard, the lever cannot pivot when a force is exerted on the distal end, for example, by tongues exerting a force on the distal end of the lever when they overlap the ledge and press the distal end inwards. Thus the lever, preferably in the form of a beam, will be tensioned due to the position of the guard.

Such beam may be connected at the middle thereof to a medicament container holder by two pivot arms so that a proximal end and a distal end of the beam are defined. The beam may be formed integral with the medicament delivery container or pivotally engaged therewith. The distal end of the beam may be arranged with a transversally extending ledge extending on both sides of the beam. The guard may be arranged such in relation to the beam that the tongues are positioned on each side of the beam.

When the guard overlaps the lever in the manner described, the guard preferably exerts a force on the distal portion of the lever and/or tensions the lever. In response, the lever—being sufficiently flexible—preferably is bent or deflected such that it does not abut the actuation locking member anymore. The lever preferably no longer abuts the actuation locking member when the guard reaches a distal position. The guard preferably reaches the distal position when the medical delivery device is correctly positioned at the dose delivery site. The distal position preferably is a position in which the guard is positioned such that the medicament delivery member can deliver a dose if the medicament delivery device is actuated.

When the lever does not abut the actuation locking member any longer due to being bent or deflected or pivoted, the actuation locking member preferably can move in at least a certain direction in which the lever restricts movement as long as it abuts the actuation locking member. Preferably, the actuation locking member can be moved in a proximal direction. When the movement of the actuation locking member is not restricted at least a certain direction, preferably the proximal direction, the medical delivery device preferably can be actuated. More preferably, the device can be actuated by activating the actuation mechanism.

When the actuation locking member can be moved in a proximal direction, preferably also a member of the actuation mechanism can move. When move, the member of the actuation mechanism preferably slides along the arms of the connection means such that the at least one arms of the connection means is free to move through at least one recesses of the member of the actuation mechanism in a radial direction. This preferably causes the hooks of the connection means to move out of contact or its resilient engagement with the cut-outs of the spring-loaded plunger member or the spring-loaded plunger rod. This preferably releases the spring-loaded plunger member or the spring loaded plunger rod to move in the proximal direction due to the force of the compressed spring of the medicament delivery drive unit. The movement of the spring-loaded plunger member or the spring loaded plunger rod then may force the stopper to move proximally and thereby expel the medicament through the medicament delivery member. The medicament delivery operation may be completed when the stopper has reached its end position, for example the proximal end position inside the medicament container. The arms of the connection means may be configured such that the push button is locked in a proximal and depressed position when the device has been actuated. For example, the member of the actuation mechanism may have at least one recess through which the at least one arm of the connection means extends and engages the push button.

When the guard is moved, preferably when the guard is moved to the distal position, the guard or the member moved by the guard preferably contacts and/or overlaps certain portions of the lever but does not contact and/or overlap the entire lever. In particular, the guard preferably does not contact and/or overlap the entire second portion of the lever. The guard may have distally extending tongues and/or portions of different radial thickness. Preferably, the guard has two distally extending tongues. The tongues may be attached to or made integral with the distal end of the guard. For example, the tongues extend in longitudinal direction towards the distal end of the device like the legs of a U. The lever may have the shape of a beam having a proximal end and a distal end. Preferably, at least a part of the second portion of the lever is provided at or close to the distal end of the lever. More preferably, the lever is thicker at or close to the distal end and, most preferably, the lever has a transversally extending ledge positioned at or close to the distal end. The ledge may extend transversally (relative to the longitudinal axis of the beam or medicament delivery device) to both sides of the beam.

According to any embodiment of the present invention, the lever may also be overlapped by a member upon actuation of the device. Preferably, the lever is overlapped by the actuation locking member. More preferably, the lever is overlapped by the actuation locking member moving into a direction in which the lever restricts its movement when it is in the initial position. Most preferably, the lever is overlapped by the actuation locking member moving in the proximal direction.

The member overlapping the lever when the device is actuated preferably overlaps at least a part of the second portion of the lever. More preferably, the member overlaps at least a part but not the entire second portion of the lever. Most preferably, the member overlaps and/or contacts a part of the second portion of the lever not being overlapped by the guard or a member moved by the guard when the guard is in the distal position. The member overlapping the lever upon actuation of the device, preferably the actuation locking member, may have one or several longitudinally extending tongues and/or portions of different radial thickness. Preferably, the proximal portion of the actuation locking member is ring-shaped (such as a sleeve-like structure) or a ring-shaped member, allowing the actuation locking member to slide along the medicament container holder. Preferably, one or several longitudinally extending tongues or extensions in proximal direction are provided at the proximal end of the actuation locking member. The tongues may be attached to or made integral with the proximal end of the actuation locking member. More preferably, one tongue is provided.

Alternatively, two tongues or three tongues are provided. The actuation locking member preferably is adapted to overlap and/or contact other parts of the lever than those contacted by the guard or a member moved by the guard. Most preferably, the longitudinally extending tongues of the actuation locking member and of the guard are adapted for the actuation locking member and the guard or a member moved by the guard being slit into each other. Seen in circumferential direction of the medicament delivery device, the tongues of the actuation locking member have a space or gap inbetween, and the tongues of the guard are also spaced from each other by a gap. Relative to each other, the tongues of the actuation locking member are in circumferential positions corresponding to the circumferential positions of the gaps between the tongues of the guard so that tongues extend into corresponding gaps.

In other words, the ring-shaped part or member of the actuation locking member may have at least one proximally extending tongue arranged in line with the beam of the locking mechanism. The ring-shaped member may further be arranged with distally directed arms. The distal parts of the arms may extend into longitudinal grooves of a guide sleeve of the actuation mechanism. At the distal end of these longitudinal grooves, transversal grooves may be arranged. A further member of the actuation mechanism may be provided inside the guide sleeve. The member may comprise a generally tubular proximal part arranged with protrusions on its outer surface, these protrusions fitting into the grooves of the guide sleeve. Further, the tubular part of the member may extend in the distal direction into a push button, which protrudes through an opening at the distal end of the device.

Thus, when the lever or beam of the locking mechanism is in the initial position, the push button may not be depressed because the proximally directed tongue of the actuation locking member abuts against the ledge of the beam and is restricted from moving in the proximal direction. Since the distal ends of the arms are placed in the longitudinal grooves, they are in the way for the protrusions. Thus the actuation mechanism can not be activated and the device is locked against actuation.

According to any embodiment of the present invention, the lever may be released from tensioning when the guard or a member moved by the guard is moved in a proximal direction. Preferably, the lever is released from tensioning when the guard is moved to a proximal position. The proximal position preferably is a position in which the guard covers the medicament delivery member but no longer overlaps the lever. Preferably, the guard or the member moved by the guard is moved in a proximal direction by a spring arranged for urging the guard in the proximal direction. The spring preferably urges the guard in a proximal direction when the medical delivery device is withdrawn from the dose delivery site. When the lever is overlapped by a further member while being tensioned, preferably when the lever is overlapped by the actuation locking member while being tensioned, releasing the tensioning of the lever may lead to the lever being positioned in a final position.

Final Position

According to any embodiment of the invention, the movement of the guard may be restricted by the lever at least in a certain direction, preferably the distal direction. More preferably, the movement of the guard in the distal direction is restricted when the guard reaches a proximal position after the device has been actuated. Preferably, the lever restricts the movement of the guard when the lever is in the final position. The final position preferably is the last position of the lever in a dose delivery cycle. More preferably, the final position is a position in which the device has been actuated and a dose has been delivered. Preferably, the final position is a position in which the actuation locking member at least partly overlaps and/or contacts the lever. More preferably, the final position is a position in which the actuation locking member at least partly overlaps and/or contacts the distal portion of the lever. Most preferably, the final position is a position in which the actuation locking member at least partly overlaps the second portion of the lever. Even more preferably the final position is a position in which the actuation locking member at least partly overlaps and/or contacts a portion of the lever against which it abuts in the initial position. The final position may be a position in which the lever is pivoted in response to a force on the distal portion of the lever and/or a position that is reached when the lever is released from tensioning.

When the lever is in the final position, movement of the guard preferably is restricted by the guard or a member moved by the guard abutting against at least a portion of the lever. Preferably, the guard abuts against a proximal portion (the first portion) of the lever. More preferably, the guard abuts against a proximal end of the lever. In the final position the guard preferably abuts against a portion of the lever that it overlaps when the lever is tensioned.

Thus, the proximal movement of the spring will cause it to release the proximal end of the beam, whereby the latter will flex outwards in the radial direction due to the tension built up in the beam. The lever, preferably beam, may thus reach the final position in which the lever restricts the movement of the guard in the distal direction. The proximal end of the longitudinal beam may be positioned between the distally directed tongues of the guard, locking the guard against movement in the distal direction and allowing the device to be discarded safely.

According to any embodiment of the invention, the actuation locking member preferably abuts the lever when the lever is in the initial position and is slidable over the lever when the lever is tensioned. Furthermore, also according to any embodiment of the invention, the guard preferably is slidable over the lever when the lever is in the initial position and abuts against one of the portions of the lever when the lever is in the final position.

The locking mechanism and/or the medicament delivery device may be configured such that the guard can be unlocked in order to start a new delivery cycle. Preferably, the medicament delivery device is configured as a disposable single-use device and the guard can not be unlocked without the device being destroyed or disassembled.

The medicament delivery device may be further arranged with a technical feature to indicate and thereby inform the user when a dose delivery operation is completed. The technical feature may be arranged to generate an audible signal in response to a signal indicative of the completed delivery operation. For this purpose, at the end of the medicament delivery sequence, the distal end of the spring-loaded plunger member or the spring-loaded plunger rod may pass out the proximal end of the at least one arm of the drive spring holder. Thereby the arm and thus the ledge of the drive spring holder may be free to move radially inwards. Due to a remaining force of the spring of the medicament delivery drive unit acting on the drive spring holder, the latter may be moved in the distal direction until the drive spring holder contacts a distal inner end surface of the connection means. When the spring holder contacts the end surface, an audible signal may be produced, indicating to the user that the device may be withdrawn from the delivery site and discarded it in a safe manner.

The lever of any of the embodiments described may be a see-saw.

BRIEF DESCRIPTION OF THE DRAWINGS

The following Figures below disclose an embodiment of the invention for illustrational purposes only. In particular, the disclosure within the Figures is not meant to limit the range of protection of the invention. The embodiment shown may be modified in many ways within the scope of the claims.

DETAILED DESCRIPTION OF THE DRAWINGS

Figure 1:
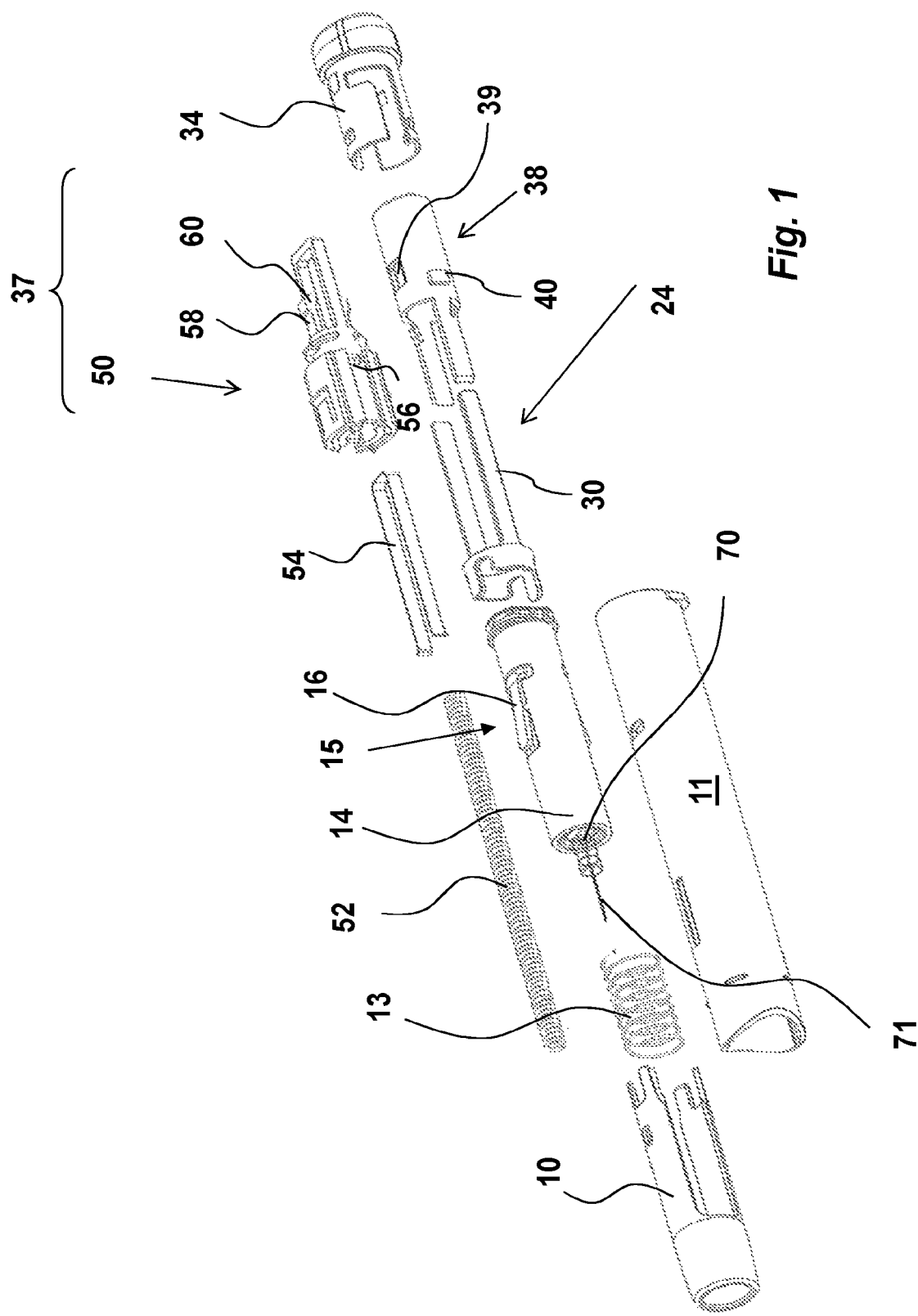
FIG. 1: Exploded view of the medicament delivery device of the present invention.

FIG. 1 shows an exploded view of a medicament delivery device according to the present invention. The device comprises a guard 10 or sleeve-like structure slidable in the longitudinal direction inside a generally cylindrical housing 11. A spring 13 may be arranged for urging the guard 10 in the proximal direction.

Figure 2:
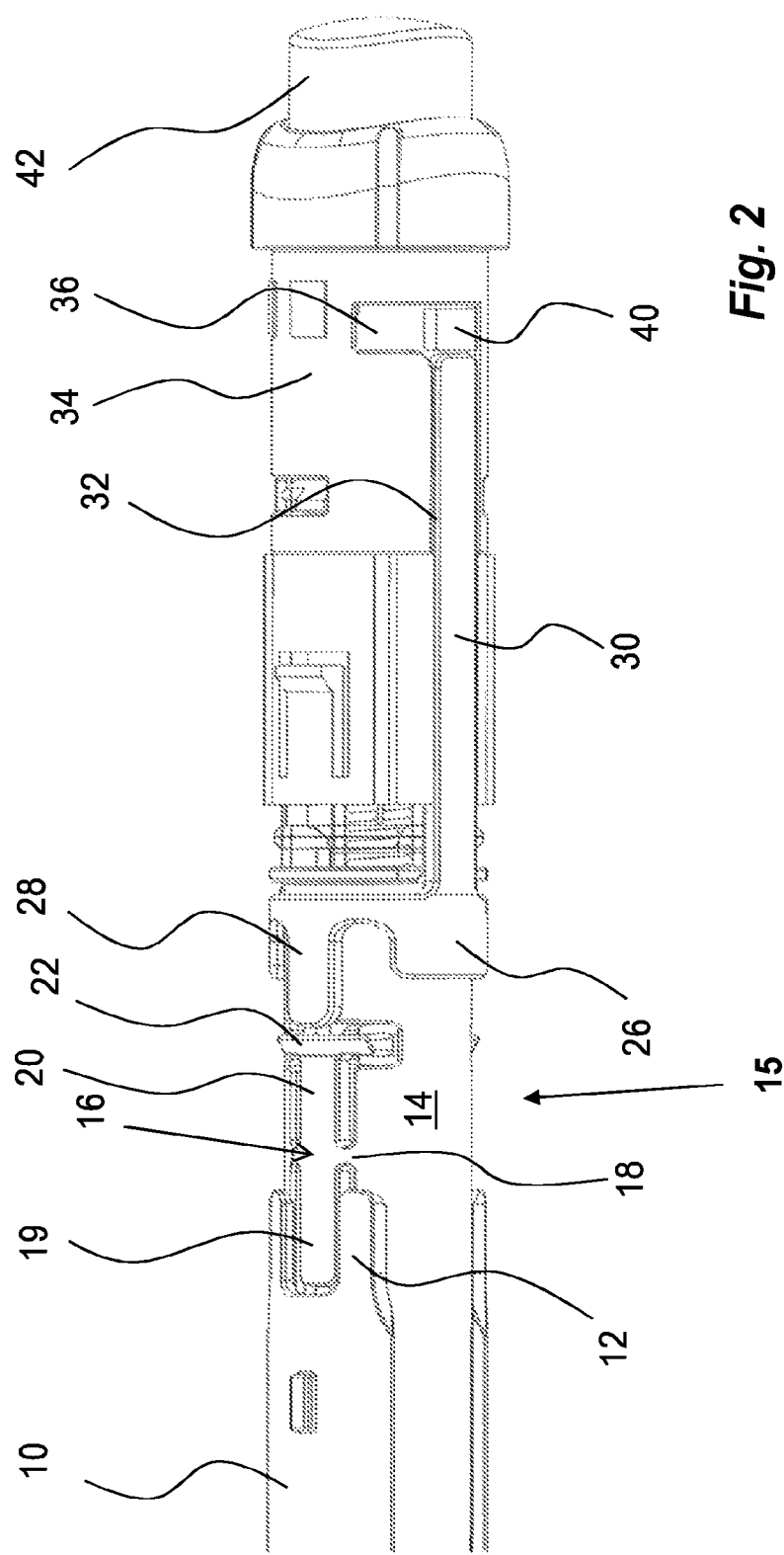
FIG. 2: Locking mechanism of a medicament delivery device of the present invention, the lever being shown in the initial position.

The guard 10 may comprise at least one distally directed tongue or may have portions of different radial thickness attached to or made integral with the distal end of the guard 10. For example, as shown in FIG. 2, the guard 10 may comprise at least two distally directed tongues 12 made integral with the distal end of the guard 10. A medicament container holder 14 for holding a medicament container 70 may be arranged in the guard 10. The medicament container may comprise a medicament delivery member. However, the medicament delivery member does not have to be part of the medicament container and may be an independent element of the device. As shown in FIG. 1, the medicament delivery member may be a needle 71.

A side surface of the medicament container holder 14 may be arranged with a locking mechanism 15. The locking mechanism 15 comprises a lever. The lever may be a see-saw. The lever may have the form of a longitudinally extending beam 16. The beam 16 may be connected at the middle thereof to the medicament container holder 14 by two pivot arms 18, creating a proximal end 19 and a distal end 20. The beam may be formed integral with the medicament delivery container 14 or pivotally engaged therewith. The distal end 20 of the beam 16 may be arranged with a transversally extending ledge 22 extending on both sides of the beam 16. The guard 10 may be arranged such in relation to the beam 16 that the tongues 12 are positioned on each side of the beam 16, as will be explained further below.

Furthermore, the device may be provided with an actuation locking member 24. The actuation locking member 24 may comprise a generally ring-shaped or sleeve-shaped member 26 surrounding the medicament container holder 14 and positioned distally in relation to the beam 16. The ring-shaped member 26 may have at least one proximally extending tongue 28 arranged in line with the beam 16. The ring-shaped member 26 may further be arranged with distally directed arms 30. As shown in FIG. 2, the distal parts of the arms 30 may extend into longitudinal grooves 32 of a guide sleeve 34. A member 38 of an actuation mechanism 37 may be provided inside the guide sleeve 34. The member 38 may comprise a generally tubular proximal part arranged with protrusions 40 on its outer surface, protrusions 40 fitting into the groove 32 of the guide sleeve 34. Further, the tubular part of the member 38 may extend in the distal direction forming a push button 42, which protrudes through an opening at the distal end of the guide sleeve 34.

The actuation mechanism 37 may further comprise a medicament delivery drive unit 50 having an plunger member or an elongated plunger rod (not shown). The plunger member may be provided with a hollow space into which a drive spring 52 is arranged to spring-load the plunger. The proximal end of the elongated plunger rod may be in contact with a stopper of the medicament container 70. The medicament delivery drive unit further may comprise a drive spring 52 acting on the plunger rod. A distal end of the spring may be in contact with a drive spring holder 54 having a general U-shape.

The drive spring holder 54 may have distally directed legs and each leg may comprise a radial outwardly extending ledge. The drive spring holder 54 may be configured to partially surround the spring-loaded plunger member.

The medicament delivery drive unit may further comprise connection means 56. The connection means 56 may be arranged with two distally directed arms 58, which may be flexible in the radial direction. The distal ends of the arms 58 may be arranged with inwardly directed hooks 60. The hooks 60 may be designed to fit into cut-outs of the plunger rod to hold it in position, as will be explained. The drive spring holder 54 may be axially arranged by the connection means 56. The member 38 may be co-axially slidable on the connection means 56.

When the medicament delivery drive unit is assembled, the spring 52 may be compressed between a proximal inner end surface of the plunger member and a transversal contact end of the drive spring holder 54. The radial outwardly extending ledges of the of the drive spring holder 54 may be engaged to the proximal annular surface of the connection means 56 for preventing the drive spring holder from being moved in the distal direction by the drive spring. The member 38 may be arranged surrounding said distally directed arms 58 such that the hooks 60 are engaged in a corresponding engagement with a cut-out on said spring-loaded plunger member.

As shown in FIG. 2, when the lever of the locking mechanism 15 is in the initial position, the push button 42 may not be depressed because the proximally directed tongue 28 of the actuation locking member 24 abuts against the ledge 22 of the beam 16 and is restricted from moving in the proximal direction. Since the distal ends of the arms 30 are placed in the longitudinal grooves 32, they are in the way for the protrusions 40. Thus the member 38 cannot be activated and the device is locked against actuation.

The next step is to perform a dose delivery. This is done by pressing the proximal end of the guard 10 against a dose delivery site. This causes the guard 10 to slide in the distal direction of the device, whereby the distally directed tongues 12 will be moved in contact with the ledge 22. Since the ledge 22 has a wedge-shape, the tongues 12 will slide onto the ledge 22. Alternatively, also only the tongues 12 or the ledge 22 and the tongues 12 can have a wedge-shape. As shown in FIG. 4, the guard 10 will overlap the ledge 22 when it reaches a distal position, exerting a force on the ledge 22 and thus on the distal end 20 of the beam 16. For example, the guard 10 may press the ledge 22 inwards. As visible best in FIG. 3, the medicament container holder 14 may be provided with a cut-out for this purpose.

As shown in FIG. 4, the guard 10 may be configured such that it also overlaps a proximal portion of the lever, preferably, such that it also overlaps the proximal end 19 of the beam 16. For example, the guard may be positioned radially outside the proximal end 19 of the beam 16. Since the proximal portion of the lever is overlapped by the guard, the lever cannot pivot when a force is exerted on the distal end, for example, by tongues 12 exerting a force on the distal end 20 of the lever when they overlap ledge 22 and press the distal end 20 inwards. Thus the lever, preferably beam 16, will be tensioned due to the position of the guard 10.

Figure 3:
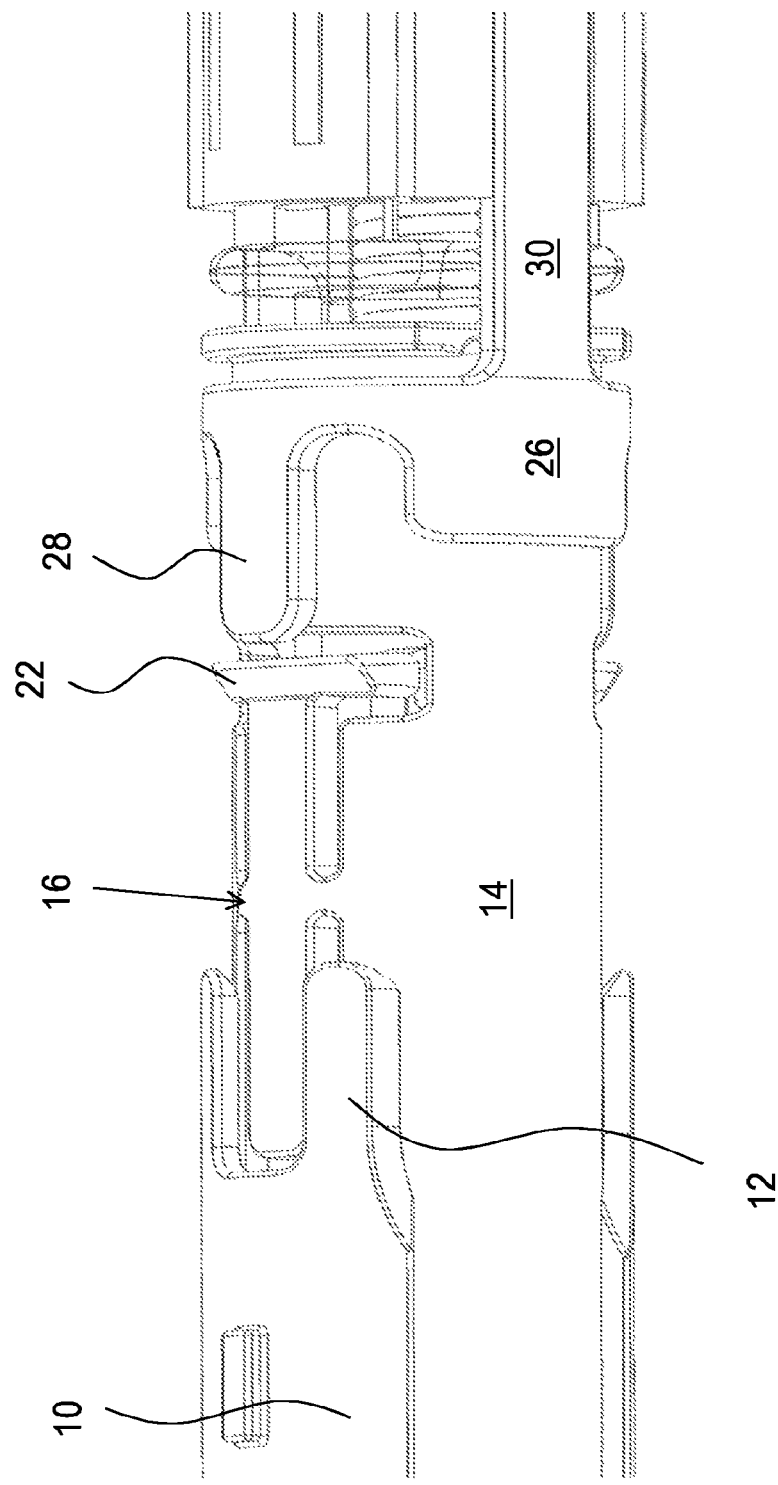
FIG. 3: Enlarged view of the locking mechanism, the lever being shown in the initial position.
Figure 4:
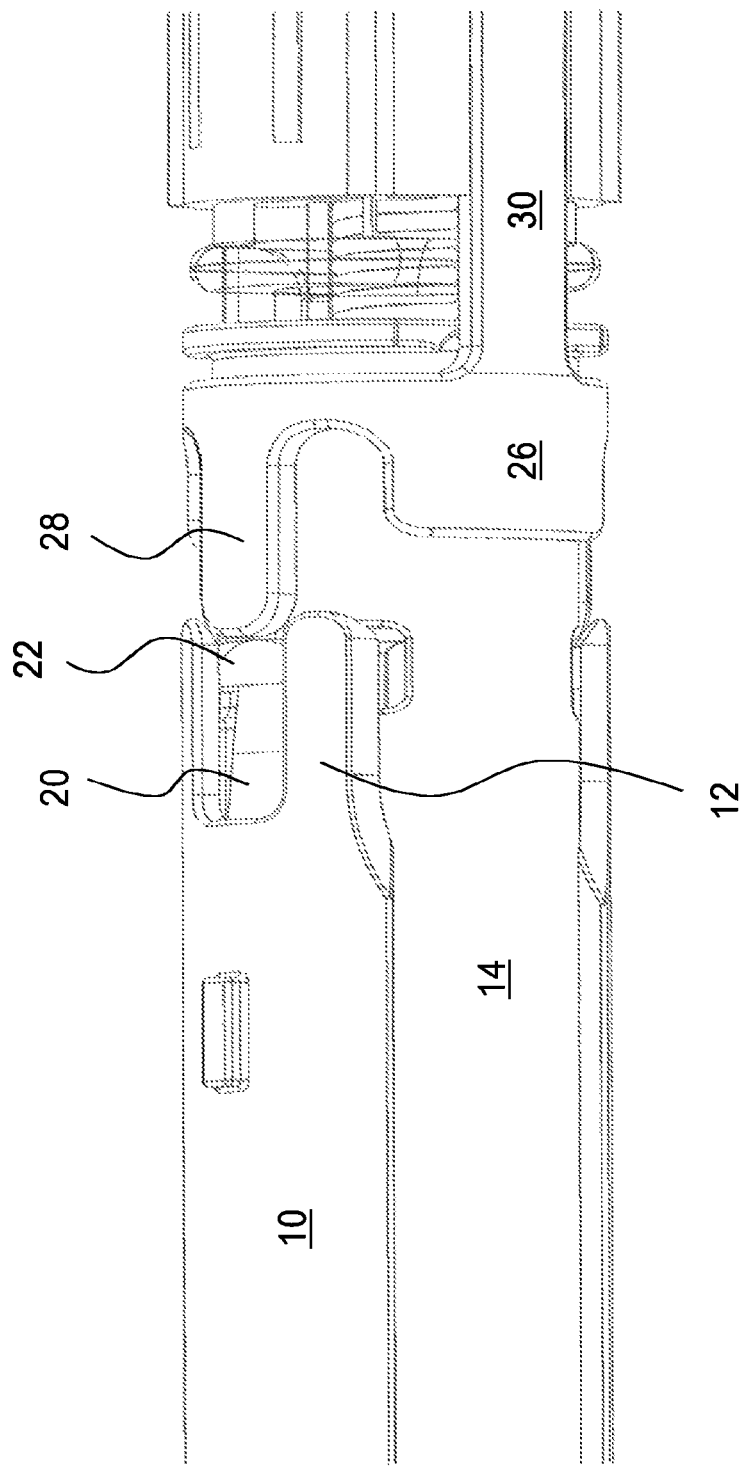
FIG. 4: Locking mechanism of a medicament delivery device of the present invention, the lever being tensioned and overlapped by the guard.

When the ledge 22 has been moved radially inwards as shown in FIG. 3, the proximally directed tongue 28 of the actuation locking member 24 does not abut the ledge. The actuation locking member 24 is free to be moved in the proximal direction. Thus, a dose of medicament can be delivered by the push button 42 being pressed in the proximal direction, whereby the protrusions 40 will push the arms 30 and thus the ring-shaped member 26 in the proximal direction, FIG. 4. This movement of the push button may cause an activation of the medicament delivery drive unit such that the ledges 60 of the arms 58 are moved out of contact with the plunger rod. The plunger rod may then be forced in the proximal direction by the spring 52 and may act on the stopper inside the medicament container 70 for delivering a dose of medicament through the medicament delivery member at the dose delivery site. The proximal movement of the ring-shaped member 26 causes its proximally directed tongue 28 to move in the proximal direction, whereby it may be moved over the ledge 22, since the latter is pressed inwards in the radial direction. Actuation locking means (not shown) may be arranged to lock the member 38 and thus the push button 42 in the proximal and depressed position.

When performing the delivery, the proximal movement of the member 38 causes it to slide along the arms 58. The arms 58 may then be free to move in the outwardly radial direction into a through recess 39 on the member 38, which causes the hooks 60 to move out of contact or its resilient engagement with the cut-outs of the spring-loaded plunger member. This in turn releases the spring-loaded plunger member to move in the proximal direction due to the force of the compressed drive spring 52. The movement of the spring-loaded plunger rod forces the stopper to move proximally and thereby expel the medicament through the medicament delivery member. When the stopper has reached its end position, i.e. the proximal end position, inside the medicament container, the medicament delivery operation is completed. The connection of the arms 58 and the through recess 39 may provide the member 38 and thus the push button 42 to be locked in a proximal and depressed position.

Figure 5:
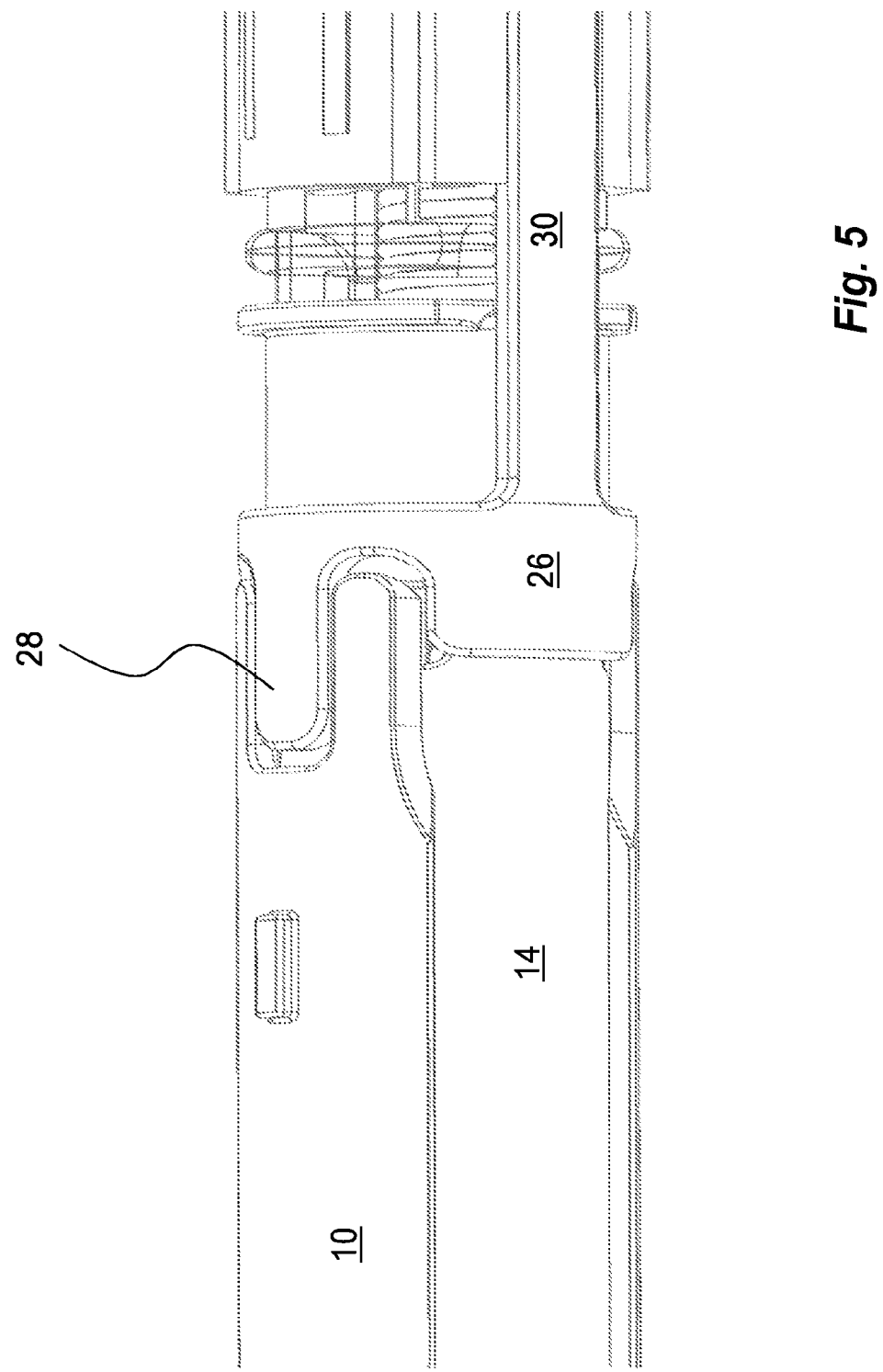
FIG. 5: Locking mechanism of the medicament delivery device of the present invention, the lever being overlapped by the guard and the actuation locking member.
Figure 6:
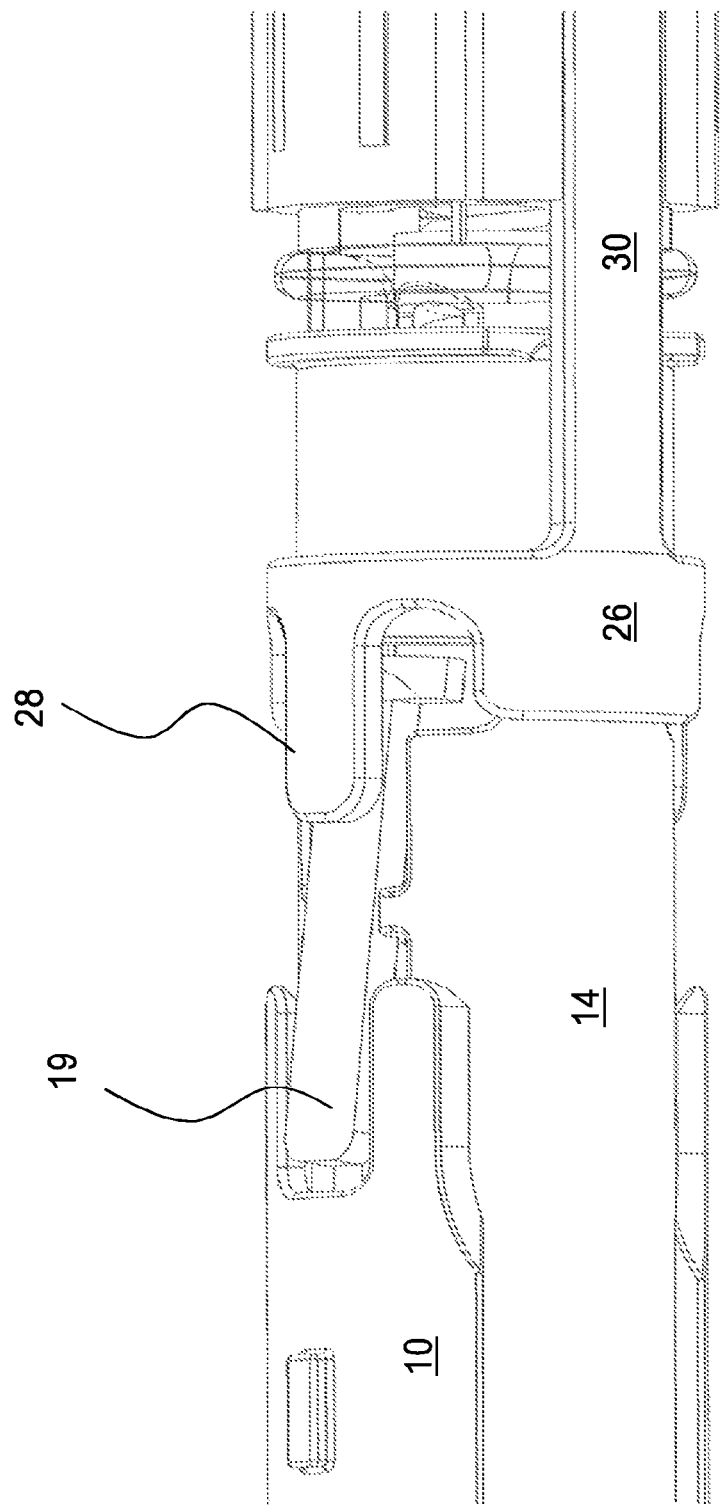
FIG. 6: Locking mechanism of the medicament delivery device of the present invention, the lever being in the final position.

When the dose has been delivered, the device may be withdrawn from the dose delivery site. This in turn may cause the guard 10 to be moved in the proximal direction by the spring 13. The proximal movement of the spring 13 will cause it to release the proximal end 19 of the beam 16, whereby the latter will flex outwards in the radial direction due to the tension built up in the beam 16. The lever, preferably beam 16, may thus reach the final position shown in FIG. 5 in which the lever restricts the movement of guard 10 in the distal direction. The proximal end 19 of the longitudinal beam 16 may be positioned between the distally directed tongues 12 of the guard 10, locking the guard 10 against movement in the distal direction and allowing the device to be discarded safely.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medicament delivery device, comprising:
a guard movable between a proximal position and a distal position;
an actuation locking member;
a medicament container holder arranged within the guard; and
a locking mechanism comprising a lever, wherein a proximal end of the lever directly contacts the guard to thereby restrict movement of the guard in the proximal position after actuation of the medicament delivery device, wherein the lever is pivotally mounted directly to the medicament container holder such that the lever pivots around a pivot axis of the lever in two directions, wherein the lever is connected to the medicament container holder by a first pivoting arm extending between the medicament container holder and a first side of the lever and a second pivoting arm extending between the medicament container holder and a second side of the lever to thereby define the proximal end of the lever and a distal end of the lever.

2. The medicament delivery device of claim 1, wherein the lever comprises a see-saw.

3. The medicament delivery device of claim 1, wherein the actuation locking member surrounds the medicament container holder.

4. The medicament delivery device of claim 1, wherein the lever is formed integral with the medicament container holder.

5. The medicament delivery device of claim 1, wherein the actuation locking member is a ring-shaped or sleeve-shaped member surrounding the medicament container holder.

6. The medicament delivery device of claim 1, wherein the lever is connected to a middle portion of the medicament container holder.

7. The medicament delivery device of claim 1, wherein the guard comprises at least two distally directed tongues.

8. The medicament delivery device of claim 7, wherein a first distally directed tongue of the at least two distally directed tongues is positioned on the first side of the lever, and wherein a second distally directed tongue of the at least two distally directed tongues is positioned on the second side of the lever.

9. The medicament delivery device of claim 1, wherein the lever has at least one first portion that is positioned closer than at least one second portion to a plane that is generally parallel to a longitudinal axis of the medicament delivery device, and wherein the plane includes the pivot axis of the lever about which the lever pivots when the lever is in an initial position.

10. The medicament delivery device of claim 9, wherein the at least one first portion is at least partly provided proximal of the at least one second portion.

11. The medicament delivery device of claim 10, wherein the at least one first portion is at least partly provided proximal of the pivot axis of the lever and the at least one second portion is at least partly provided distal of the pivot axis of the lever.

12. The medicament delivery device of claim 9, wherein at least a part of the at least one first portion and at least a part of the at least one second portion are overlapped by the guard when the guard is moved in a distal direction.

13. The medicament delivery device of claim 9, wherein at least a part of the at least one second portion is overlapped by the actuation locking member when the actuation locking member is moved in a proximal direction.

14. The medicament delivery device of claim 9, wherein the at least one second portion of the lever is thicker than the at least one first portion of the lever.

15. The medicament delivery device of claim 1, wherein the lever is put in a tensioned state by the guard when the guard is moved in a distal direction.

16. The medicament delivery device of claim 1, wherein the guard and the actuation locking member are configured to contact less than the entire lever.

17. The medicament delivery device of claim 1, wherein the actuation locking member comprises at least one proximally extending tongue, and wherein the at least one proximally extending tongue is positioned distal to and aligned with the lever when the guard is in the proximal position.

18. The medicament delivery device of claim 1, wherein the actuation locking member is positioned adjacent to the guard when the guard is in the proximal position such that the lever does not limit movement of the actuation locking member.

19. The medicament delivery device of claim 1, wherein the lever restricts movement of the guard when pivoting in response to a force on a distal portion of the lever.

* * * * *